US012746289B2

(12) United States Patent
Wang et al.

(10) Patent No.: US 12,746,289 B2
(45) Date of Patent: Sep. 29, 2026

(54) ANTITUMOR PHARMACEUTICAL COMPOSITION AND USE THEREOF

(71) Applicant: JENKEM TECHNOLOGY CO., LTD. (TIANJIN), Tianjin (CN)

(72) Inventors: Qingbin Wang, Tianjin (CN); Juan Shi, Tianjin (CN); Jingyun Hu, Tianjin (CN); Xuan Zhao, Tianjin (CN)

(73) Assignee: JENKEM TECHNOLOGY CO., LTD. (TIANJIN), Tianjin (CN)

( * ) Notice: Subject to any disclaimer, the term of this patent is extended or adjusted under 35 U.S.C. 154(b) by 557 days.

(21) Appl. No.: 18/252,424

(22) PCT Filed: Nov. 8, 2021

(86) PCT No.: PCT/CN2021/129184

§ 371 (c)(1),
(2) Date: May 10, 2023

(87) PCT Pub. No.: WO2022/100535

PCT Pub. Date: May 19, 2022

(65) Prior Publication Data

US 2023/0405132 A1 Dec. 21, 2023

(30) Foreign Application Priority Data

Nov. 10, 2020 (CN) ........................ 202011251434.0

(51) Int. Cl.
*A61K 47/60* (2017.01)
*A61K 31/4188* (2006.01)
*A61P 35/00* (2006.01)

(52) U.S. Cl.
CPC .......... *A61K 47/60* (2017.08); *A61K 31/4188* (2013.01); *A61P 35/00* (2018.01)

(58) Field of Classification Search
CPC ...... A61K 47/60; A61K 31/4188; A61P 35/00
See application file for complete search history.

(56) References Cited

FOREIGN PATENT DOCUMENTS

| | | | | |
|---|---|---|---|---|
| CN | 103083680 A | 5/2013 | | |
| CN | 104524588 A | 4/2015 | | |
| CN | 112263579 A | 1/2021 | | |
| WO | 0154678 A2 | 8/2001 | | |
| WO | WO-2010148163 A1 | * 12/2010 | ............ | A61K 41/00 |

OTHER PUBLICATIONS

Gura et al., Systems for Identifying New Drugs are Often Faulty. Science, New Series, (1997), 278(5340), 1041-1042 (Year: 1997).*
Johnson et al., Relationships between drug activity in NCI preclinical in vitro and in vivo models and early clinical trials. British Journal of Cancer, (2001), 84(10), 1424-1431 (Year: 2001).*
Martino et al., The long story of camptothecin: From traditional medicine to drugs, Bioorganic & Medicinal Chemistry Letters, (2017), 27(4), 701-707 (Year: 2017).*
Palmerini et al., "Irinotecan and temozolomide in recurrent Ewing sarcoma: an analysis in 51 adult and pediatric patients", Acta Oncologica, Mar. 13, 2018, 8 pages.
Liu et al., "Study on the relationship between the hypermethylation state of MGMT in SK-N-SH induced by temozolomide and irinotecan sensitivity", Anti-tumor Pharmacy, Apr. 2011, vol. 1, No. 2, 8 pages.
Xu et al.,. "Efficacy and Safety of Temozolomide in Combination with Irinotecan in Non-Small Cell Lung Cancer Patients with Relapsed/refractory Brain Metastasis", Clinical Medication Journal, Sep. 2014, vol. 12, No. 5, 8 pages.
Liu et al., "Clinical efficacy of irinotecan and temozolomide in treatment of refractory and recurrent child medulloblastoma", Shandong Medical Journal, 2019, vol. 59, No. 12, 8 pages.
International Search Report for PCT/CN2021/129184 mailed Jan. 27, 2022, 10 pages.
Written Opinion of the ISA for PCT/CN2021/129184 mailed Jan. 27, 2022, 6 pages.

* cited by examiner

*Primary Examiner* — Renee Claytor
*Assistant Examiner* — Christopher Lindsay Johnson
(74) *Attorney, Agent, or Firm* — NIXON & VANDERHYE, PC

(57) ABSTRACT

An antitumor pharmaceutical composition and an application thereof. Active ingredients of the antitumor pharmaceutical composition contain a polyethylene glycol-modified camptothecin derivative (in particular, polyethylene glycol-modified irinotecan) and temozolomide. It is proved by means of animal experiments that the administration of polyethylene glycol-modified camptothecin derivative (in particular, polyethylene glycol-modified irinotecan) and temozolomide in combination has an extremely strong treatment effect on tumors (such as neuroblastoma), and the tumor inhibition rate can reach 98% and is significantly superior to that of a monotherapy group; thus, the provided antitumor pharmaceutical composition has better application prospects for treatment of tumors.

9 Claims, 3 Drawing Sheets

ANTITUMOR PHARMACEUTICAL COMPOSITION AND USE THEREOF

CROSS-REFERENCE TO RELATED APPLICATION

This application is the U.S. national phase of International patent application No. PCT/CN2021/129184, filed on Nov. 8, 2021, which claims the benefit and priority of Chinese patent application No. CN202011251434.0, filed on Nov. 10, 2020, the content of each of which is incorporated herein by reference in its entirety and for all purposes.

TECHNICAL FIELD

The present invention relates to the technical field of pharmaceuticals, and particularly to an antitumor pharmaceutical composition comprising polyethylene glycol-modified camptothecin derivatives (particularly polyethylene glycol-modified irinotecan) and temozolomide as active ingredients, and use thereof.

BACKGROUND

Tumor is one of the common diseases that threaten human health, second only to cardiovascular diseases. Despite significant progress in cancer research and the development of various methods for treating tumors, such as radiotherapy and chemotherapy, existing drugs and therapies have limitations in radical treatment, which can easily lead to drug resistance and side effects. The mortality rate of tumor ranks first among all the human diseases. Data shows that tumor caused 3 million deaths in China in 2006, as well as an increase in morbidity and an ascending proportion in younger population. According to data statistics, the morbidity of tumors in China has increased by 69% and mortality has increased by 29.4% in less than 20 years. Therefore, developing new and powerful anti-tumor therapeutic drugs remains the main direction of current cancer treatment.

Camptothecin (CPT), a pyrroloquinoline cytotoxic alkaloid, is one of the natural antitumor drugs of top interest except for paclitaxel. From 1967 to 1970, researchers found that the alkaloid shows high antitumor activity in Hela cells, L1210 cells and rodents in vitro, which drew great attention. In 1985, Hsiang et al found that camptothecin and its derivatives exert the anticancer function by targeting topoisomerase (topo) to inhibit DNA synthesis. After that many derivatives were found and the compound became a new focus of study in the anticancer field. To date, a series of semi-synthetic and fully synthetic camptothecin derivatives have been found and entered clinical application or clinical trials, such as hydroxycamptothecin, irinotecan, topotecan, 9-aminocamptothecin, 9-nitrocamptothecin, gimatecan and the like. Use of camptothecin derivatives in treating neuroblastoma, particularly recurrent and refractory neuroblastomas, has been reported, which, however, exhibited unsatisfactory results.

SUMMARY

To overcome the defects in the prior art, the present invention provides a pharmaceutical composition, which comprises the following as active ingredients:

(1) a polyethylene glycol-modified camptothecin derivative or a pharmaceutically acceptable salt, ester, prodrug, or solvate thereof; and (2) temozolomide or a pharmaceutically acceptable salt, ester, prodrug, or solvate thereof.

In one embodiment of the present invention, the active ingredients described above consist of the aforementioned (1) and (2).

Specifically, the active ingredients described above may consist of a polyethylene glycol-modified camptothecin derivative and temozolomide.

Specifically, in the pharmaceutical composition described above, the active ingredients (2) and (1) (e.g., temozolomide to a polyethylene glycol-modified camptothecin derivative) may be present in a mass ratio of (0.1-10):(0.1-10) (such as 1:0.1, 1:0.2, 1:0.3, 1:0.4, 1:0.5, 1:1, 1:1.5, 1:2, 1:2.5, 1:3, 1:4, 1:5, 1:6, 1:7, 1:8, 1:9, or 1:10), and particularly 1:(1-10), such as 1:(1-5).

Specifically, in the pharmaceutical composition described above, the camptothecin derivative moiety and temozolomide may be present in a molar ratio of (0.01-100):(0.01-100) (such as 1:0.1, 1:1, 1:10, 1:20, 1:30, 1:40, 1:50, 1:70, 1:80, 1:90, or 1:100).

Specifically, the polyethylene glycol-modified camptothecin derivative described above in the present invention has a structure shown in general formula (I):

(I)

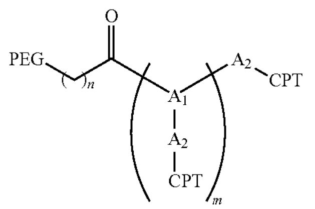

wherein,

PEG represents a polyethylene glycol residue with a molecular weight of 300 to 60000 Daltons (such as 300, 500, 1000, 2000, 3000, 4000, 5000, 6000, 7000, 8000, 9000, 10000, 16000, 17000, 18000, 19000, 20000, 21000, 22000, 23000, 24000, 25000, 26000, 28000, 30000, 40000, 50000, or 60000 Daltons);

$A_1$ and $A_2$ represent the same or different amino acid residues;

m is an integer of 2 to 12 (such as 2, 3, 4, 5, 6, 7, 8, 9, 10, 11, or 12);

n is an integer of 0 to 6 (such as 0, 1, 2, 3, 4, 5, or 6); and

CPT is a camptothecin derivative residue.

Specifically, m is an integer of 2 to 6, for example, 2 or 3.

Specifically, n is an integer of 0 to 3, for example, 0, 1, 2, or 3.

Specifically, the camptothecin derivative described above is selected from: 10-hydroxycamptothecin, 7-ethyl-10-hydroxycamptothecin, 9-nitrocamptothecin, 9-aminocamptothecin, irinotecan, topotecan, belotecan, exatecan, lurtotecan, diflomotecan, gimatecan and karenitecin. In one embodiment of the present invention, the camptothecin derivative described above is 7-ethyl-10-hydroxycamptothecin or irinotecan.

Specifically, in the general formula (I), the CPT may be selected from the following structures:

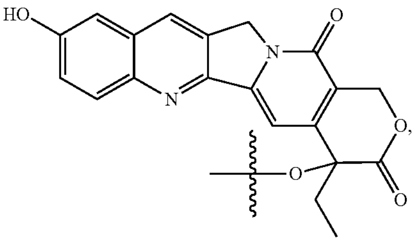
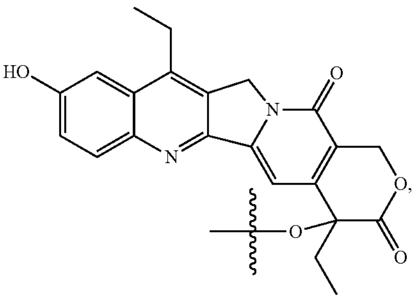
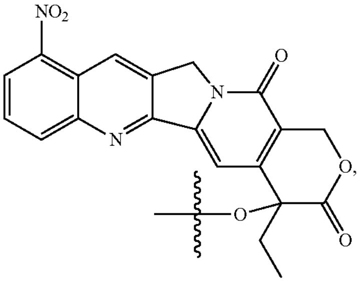
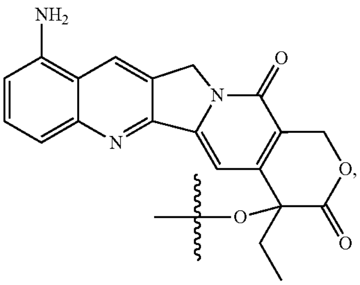
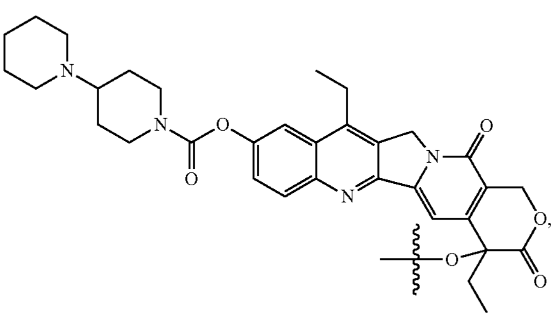
-continued
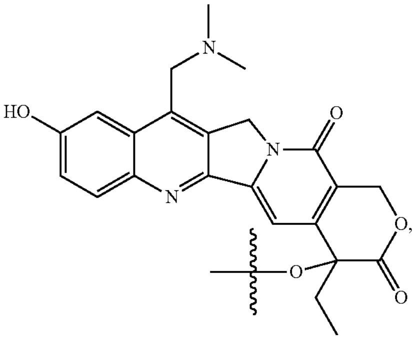
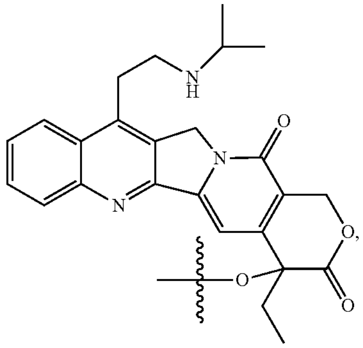
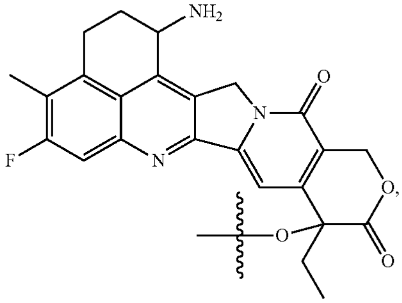
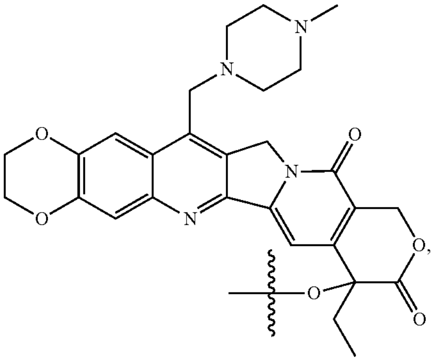
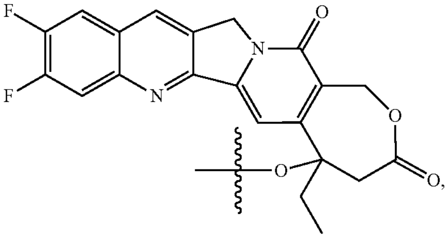

-continued

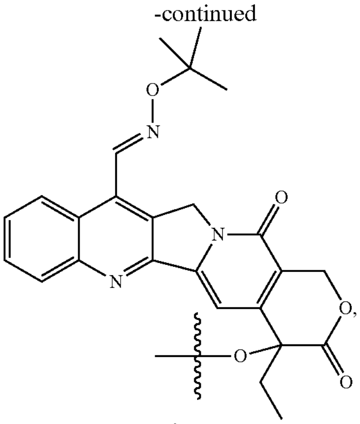

and

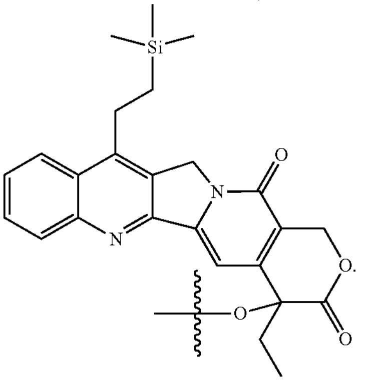

In one embodiment of the present invention, the CPT is

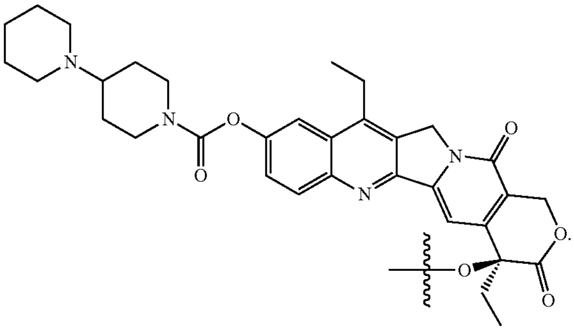 [SMILES: *O[C@]1(CC)C(=O)OCc2c1cc1n(c2=O)Cc2c-1nc1ccc(OC(=O)N3CCC(N4CCCCC4)CC3)cc1c2CC]

Specifically, the PEG described above may have a molecular weight of 10000 to 40000 Daltons, such as 15000 to 30000, 18000 to 25000, and specifically, 21000 to 23000.

Specifically, the PEG described above may be a linear, Y-shaped, or multi-branched PEG residue.

In one embodiment of the present invention, the PEG described above has a structure shown in general formula (II):

(II)

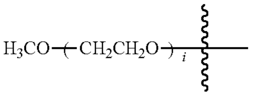

wherein i is an integer of 10 to 1500 (such as 10, 20, 30, 40, 50, 100, 200, 300, 400, 500, 600, 700, 800, 900, 1000, 1100, 1200, 1300, 1400, or 1500).

In another embodiment of the present invention, the PEG described above has a structure shown in general formula (III):

(III)

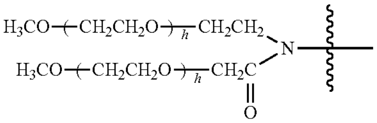

wherein, h is an integer of 5 to 700 (such as 5, 10, 20, 30, 40, 50, 100, 150, 200, 250, 300, 350, 400, 450, 500, 550, 600, 650, or 700).

In another embodiment of the present invention, the PEG described above has a structure shown in general formula (IV):

(IV)

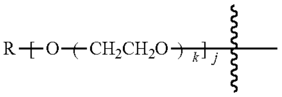

wherein,

- k is an integer of 1 to 500 (such as 1, 5, 10, 20, 30, 40, 50, 100, 150, 200, 250, 300, 350, 400, 450, or 500);
- j is an integer of 3 to 12 (such as 3, 4, 5, 6, 7, 8, 9, 10, 11, or 12); and
- R is a residue of a core molecule of a multi-branched polyethylene glycol that may be selected from: pentaerythritol, methyl glucoside, sucrose, diethylene glycol, propylene glycol, glycerol, and polyglycerol residues.

In one embodiment of the present invention, the PEG described above has a structure shown in general formula (V):

(V)

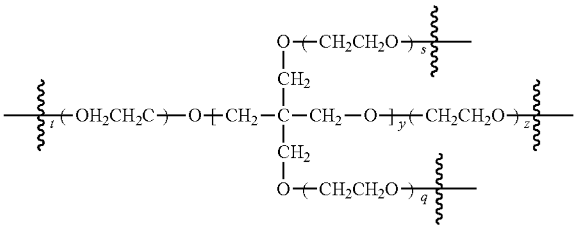

wherein, q, s, t, and z are independently selected from an integer of 2 to 340, and y is an integer of 1 to 5 (such as 1, 2, 3, 4, or 5).

In one embodiment of the present invention, the PEG described above has a structure shown in general formula (VI):

(VI)

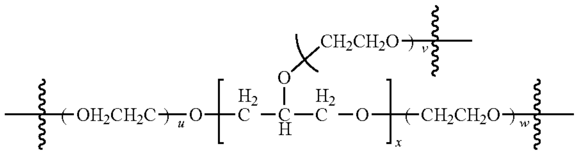

wherein, u, v, and w are independently selected from an integer of 2 to 460, and x is an integer of 1 to 5 (such as 1, 2, 3, 4, or 5).

Specifically, in the general formula (I), $A_1$ and $A_2$ are independently selected from: aspartic acid, glutamic acid, glycine, alanine, leucine, isoleucine, valine, phenylalanine, and methionine residues; and more specifically, $A_1$ is selected from aspartic acid and glutamic acid residues, $A_2$ is selected from glycine, alanine, leucine, isoleucine, valine, phenylalanine, and methionine residues. In one embodiment of the present invention, $A_1$ is glutamic acid residue, and $A_2$ is glycine residue.

Specifically, $A_1$ is

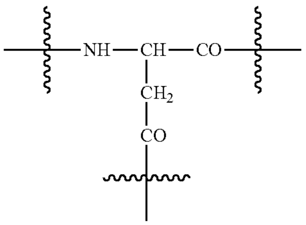

or

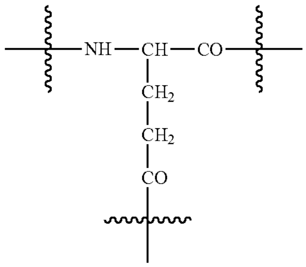

.

Specifically, $A_2$ is selected from

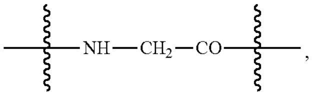

,

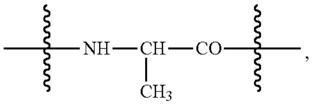

,

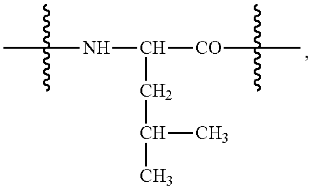

,

-continued

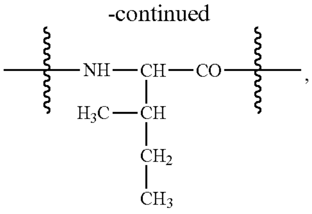

,

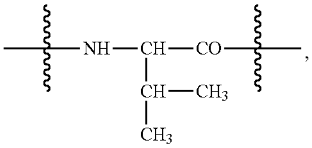

,

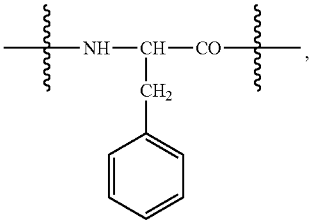

, and

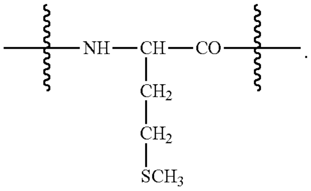

.

In one embodiment of the present invention,

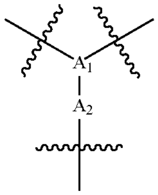

is

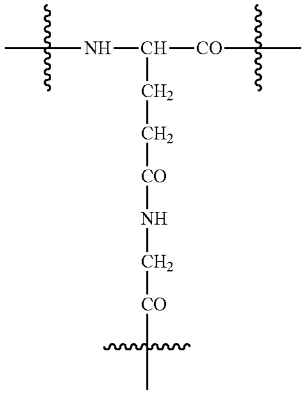

.

In one embodiment of the present invention, in the structure of general formula (I), m is 2, n is 1, and the polyethylene glycol-modified camptothecin derivative has a structure shown in general formula (VII):

(VII)

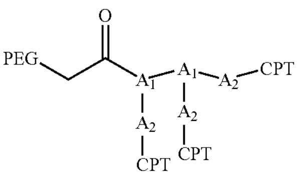

wherein, PEG, CPT, A 1, and $A_2$ have the corresponding definitions described above in the present invention.

In another embodiment of the present invention, in the structure of general formula (I), m is 3, n is 1, and the polyethylene glycol-modified camptothecin derivative described in the present invention has a structure shown in general formula (VIII):

(VIII)

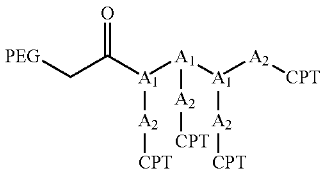

wherein, PEG, CPT, A 1, and $A_2$ have the corresponding definitions described above in the present invention.

In one embodiment of the present invention, the polyethylene glycol-modified camptothecin derivative described above has the following structure:

Specifically, the pharmaceutical composition described above may be a tablet (including dragée tablet, film coating tablet, sublingual tablet, oral disintegrating tablet, buccal tablet, etc.), a pill, a powder, a granule, a capsule (including soft capsule and microcapsule), a lozenge, a syrup, a liquid, an emulsion, a suspension, a controlled release formulation (such as instantaneous release formulation, sustained release formulation, sustained release microcapsule), an aerosol, a film (such as oral disintegrating film, oral mucosa-adherent film), an injection (such as subcutaneous injection, intravenous injection, intramuscular injection, intraperitoneal injection), an intravenous drip infusion, a transdermal formulation, an ointment, a lotion, an adhesive formulation, a suppository (such as rectal suppository, vaginal suppository), a pellet, a nasal formulation, a pulmonary formulation (inhalant), and an eye drop, etc.

Specifically, the pharmaceutical composition described above can be administered gastrointestinally or parenterally, e.g., administered through an intravenous, intramuscular, intradermal, subcutaneous, or intraperitoneal route.

(IX)

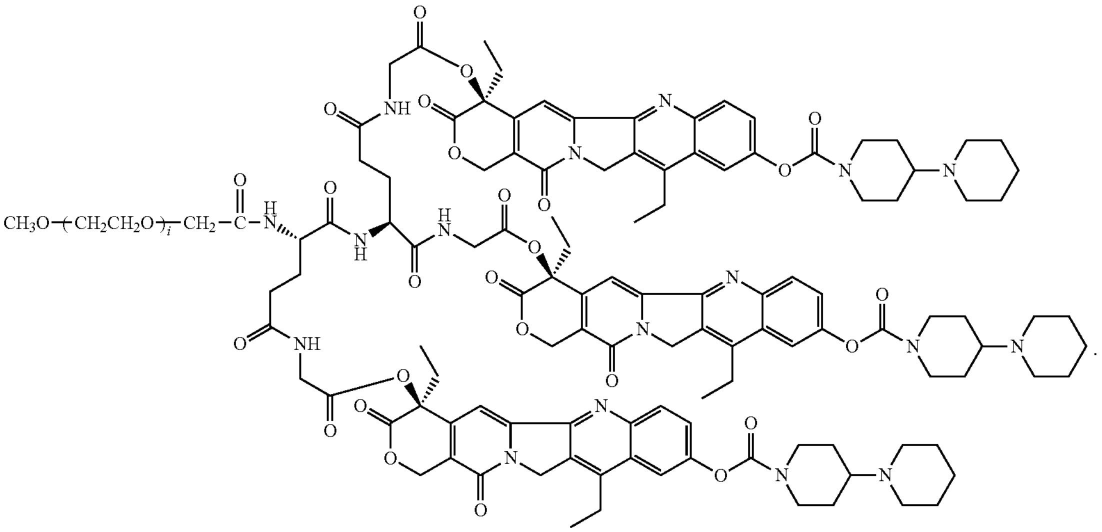

Specifically, in the above formula VII, the PEG may have a molecular weight of 10000 to 40000 Daltons, such as 15000 to 30000, 18000 to 25000, and specifically, 21000 to 23000.

Specifically, the pharmaceutical composition described above further comprises one or more pharmaceutically acceptable auxiliary materials.

Specifically, the pharmaceutically acceptable auxiliary material described above refers to a conventional pharmaceutical auxiliary material in the pharmaceutical field, such as, a diluent, an excipient such as water; a filler such as starch and sucrose, etc.; a binder such as cellulose derivatives, alginate, gelatin, polyvinylpyrrolidone, etc.; a wetting agent such as glycerol, etc.; a disintegrant such as agar, calcium carbonate, sodium bicarbonate, etc.; an absorption promoter such as quaternary ammonium compounds, etc; a surfactant such as cetanol, etc.; an adsorption carrier such as kaolin, bentonite, etc.; and a lubricant such as talc powder, calcium stearate, magnesium stearate, polyethylene glycol, etc. In addition, other adjuvants such as flavoring agents, sweetening agents, etc., can also be added to the pharmaceutical composition.

Specifically, in the pharmaceutical composition described above, the two active ingredients (the polyethylene glycol-modified camptothecin derivative or the pharmaceutically acceptable salt, ester, prodrug, or solvate thereof, and temozolomide or the pharmaceutically acceptable salt, ester, prodrug, or solvate thereof) can be administered through the same or different administration routes. For example, the polyethylene glycol-modified camptothecin derivative or the pharmaceutically acceptable salt, ester, prodrug, or solvate thereof can be administered through a parenteral route (e.g., through an intravenous, intramuscular, intradermal, subcutaneous or intraperitoneal route), and temozolomide or the pharmaceutically acceptable salt, ester, prodrug, or solvate thereof can be administered through gastrointestinal route (e.g., orally).

Specifically, in the pharmaceutical composition described above, the two active ingredients (the polyethylene glycol-modified camptothecin derivative or the pharmaceutically acceptable salt, ester, prodrug, or solvate thereof, and temozolomide or the pharmaceutically acceptable salt, ester, prodrug, or solvate thereof) can be formulated for simultaneous, separate or sequential administration.

In one embodiment of the present invention, the pharmaceutically acceptable auxiliary materials described above are pharmaceutically acceptable auxiliary materials for injection, such as isotonic sterile saline (sodium dihydrogen phosphate, disodium hydrogen phosphate, sodium chloride, potassium chloride, calcium chloride, magnesium chloride, etc., or mixtures of the above salts), or dried, e.g., freeze-dried, compositions which may be properly formed into injectable solutes by addition of sterile water or physiological saline.

Various dosage forms of the pharmaceutical composition of the present invention can be prepared according to conventional production methods in the field of pharmaceuticals. For example, the active ingredients may be mixed with one or more pharmaceutically acceptable auxiliary materials and then prepared into the desired dosage form.

Specifically, the pharmaceutical composition of the present invention may comprise 0.1% to 99.5% (such as 0.1%, 0.5%, 1%, 2%, 3%, 4%, 5%, 6%, 7%, 8%, 9%, 10%, 20%, 30%, 40%, 50%, 60%, 70%, 80%, 90%, 95%, 99%, or 99.5%) by weight of the active ingredients.

The present invention further provides use of the pharmaceutical composition described above in preparing a medicament for treating tumors.

Specifically, in the use described above, the tumor is a malignancy, including, but not limited to: lymphoma, blastoma, sarcoma, liposarcoma, synovial cell sarcoma, neuroendocrine tumor, carcinoid tumor, gastrinoma, islet cell carcinoma, mesothelioma, neurilemmoma, acoustic neuroma, meningioma, adenocarcinoma, melanoma, leukemia, squamous cell carcinoma, epithelial squamous cell carcinoma, lung carcinoma (such as small cell lung carcinoma, non-small cell lung carcinoma), adenocarcinoma lung carcinoma, squamous lung carcinoma, peritoneal carcinoma, hepatocellular carcinoma, gastric carcinoma, intestinal carcinoma, pancreatic carcinoma, glioma, cervical carcinoma, ovarian carcinoma, liver carcinoma, bladder carcinoma, liver carcinoma, breast carcinoma, colon carcinoma, rectal carcinoma, colorectal carcinoma, uterine carcinoma, salivary gland carcinoma, kidney carcinoma, prostate carcinoma, vulval carcinoma, thyroid carcinoma, liver carcinoma, anal carcinoma, penile carcinoma, Merkel cell carcinoma, esophageal carcinoma, biliary tract carcinoma, head and neck carcinoma, etc.

Specifically, the tumor described above can be selected from: a mid- and late-stage tumor, a recurrent and/or refractory tumor, a tumor refractory to and/or recurring after a chemotherapy, a tumor refractory to and/or recurring after a radiotherapy, a tumor refractory to and/or recurring after a targeted therapy, and a tumor refractory to and/or recurring after an immunotherapy.

In one embodiment of the present invention, in the use described above, the tumor is a brain tumor, such as a glioma. The glioma may include: astrocytoma, glioblastoma multiforme, ependymoma, ependymoblastoma, medulloblastoma, oligodendroglioma, and oligodendroblastoma, and particularly, adult refractory glioblastoma multiforme and recurrent or progressive glioblastoma multiforme, and anaplastic astrocytoma.

In one embodiment of the present invention, in the use described above, the tumor is a blastoma, including but not limited to: glioblastoma, medulloblastoma, neuroblastoma, hemangioblastoma, hepatoblastoma, retinoblastoma, and the like.

In one embodiment of the present invention, in the use described above, the tumor is neuroblastoma, and particularly, recurrent or refractory neuroblastoma.

The present invention further provides use of the pharmaceutical composition described above in enhancing the efficacy of a polyethylene glycol-modified camptothecin derivative (e.g., polyethylene glycol-modified irinotecan) or temozolomide.

The present invention further provides use of a polyethylene glycol-modified camptothecin derivative (e.g. polyethylene glycol-modified irinotecan) or a pharmaceutically acceptable salt, ester, prodrug, or solvate thereof in enhancing the efficacy of temozolomide.

The present invention further provides use of temozolomide or a pharmaceutically acceptable salt, ester, prodrug, or solvate thereof in enhancing the efficacy of a polyethylene glycol-modified camptothecin derivative (e.g., polyethylene glycol-modified irinotecan).

Specifically, in the use described above, the efficacy is an antitumor efficacy, such as inhibiting tumor growth (e.g., reducing tumor volume).

Specifically, the enhancement described above may be an increase of 1%, 5%, 10%, 20%, 30%, 40%, 50%, 60%, 70%, 80%, 90%, 100%, 200%, 300%, 400%, 500%, or the like in the antitumor efficacy.

Specifically, in the use described above, the polyethylene glycol-modified camptothecin derivative and the tumor have the corresponding definitions described above in the present invention.

The present invention further provides a method for treating tumor, comprising a step of administering a therapeutically effective amounts of a polyethylene glycol-modified camptothecin derivative or a pharmaceutically acceptable salt, ester, prodrug, or solvate thereof, and temozolomide or a pharmaceutically acceptable salt, ester, prodrug, or solvate thereof, or the pharmaceutical composition described above in the present invention to a subject in need thereof.

Specifically, in the method described above, the tumor, the polyethylene glycol-modified camptothecin derivative, and the pharmaceutical composition have the corresponding definition described above in the present invention.

Specifically, in the method described above, the polyethylene glycol-modified camptothecin derivative or the pharmaceutically acceptable salt, ester, prodrug, or solvate thereof, and temozolomide or the pharmaceutically acceptable salt, ester, prodrug, or solvate thereof can be administered through the same or different administration routes. For example, the polyethylene glycol-modified camptothecin derivative or the pharmaceutically acceptable salt, ester, prodrug, or solvate thereof can be administered through a parenteral route (e.g., through an intravenous, intramuscular, intradermal, subcutaneous or intraperitoneal route), and temozolomide or the pharmaceutically acceptable salt, ester, prodrug, or solvate thereof can be administered through gastrointestinal route (e.g., orally).

Specifically, in the method described above, the polyethylene glycol-modified camptothecin derivative or the pharmaceutically acceptable salt, ester, prodrug, or solvate thereof, and temozolomide or the pharmaceutically acceptable salt, ester, prodrug, or solvate thereof can be formulated for simultaneous, separate or sequential administration.

Specifically, the subject described above is a mammal, such as human.

In one embodiment of the present invention, in the method described above, the tumor is neuroblastoma, and particularly, recurrent or refractory neuroblastoma.

Specifically, the therapeutically effective amount described above may vary according to the route of administration, the age and body weight of the patient, the disease to be treated in the patient and the severity, etc., and may be administered in one or more doses.

It is founded by means of animal experiments that the combination of polyethylene glycol-modified camptothecin derivative (in particular, polyethylene glycol-modified irinotecan) and temozolomide has an extremely potent efficacy on tumors (e.g., neuroblastoma), with a tumor inhibition rate of up to 98%, significantly superior to those of single drug treatment groups. Therefore, the pharmaceutical composition provided by the present invention has better application prospects for tumor treatment.

DETAILED DESCRIPTION

Figure 1:
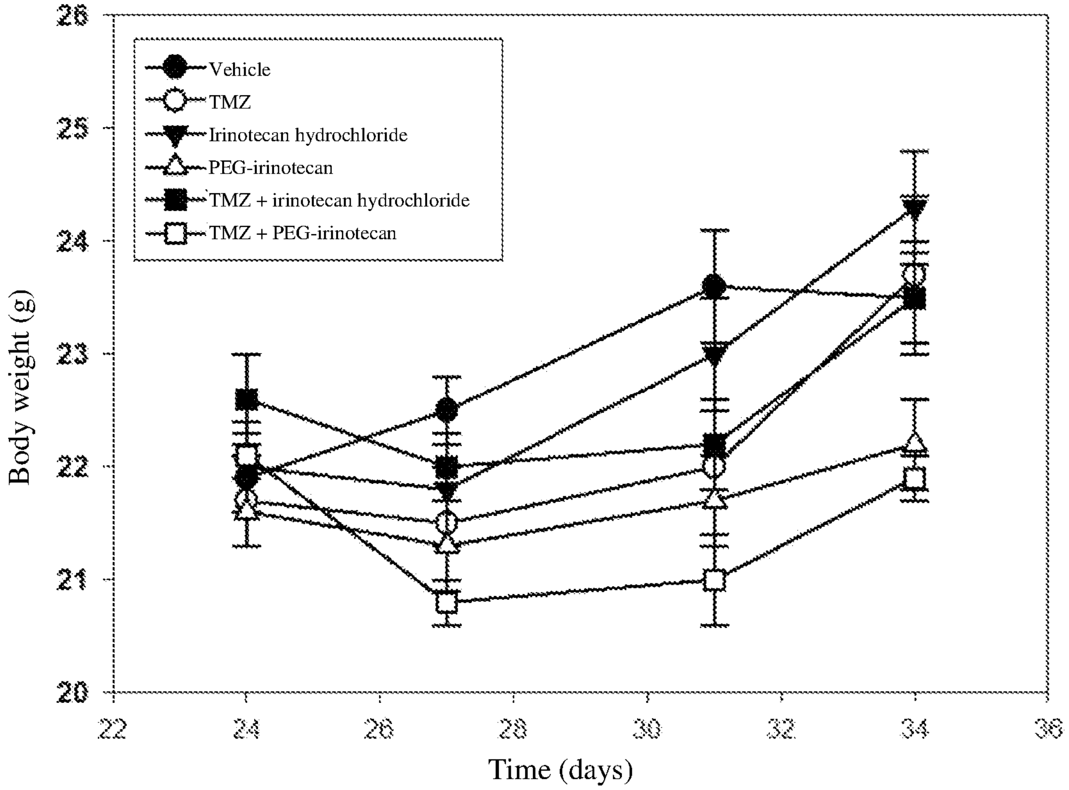
FIG. 1 shows the changes in body weight of mice in each group, wherein, the data points represent the mean body weight of the group, and the error bars represent the standard error of the mean (SEM).

Unless otherwise defined, all scientific and technical terms used herein have the same meaning as commonly understood by those skilled in the art to which the present invention relates.

In polymer chemistry, a polymer sample is often a mixture of homologs of unequal molecular weights, and thus the molecular weight has a distribution. The molecular weight used herein generally refers to average molecular weight. There are various representations of average molecular weight, and the most common ones are the number average molecular weight (Mn) and the weight average molecular weight (Mw). In the present invention, it is preferred that the polymers (e.g., polyethylene glycol) are characterized by molecular weight due to the potential inhomogeneity of the PEG compound, which is generally defined by its average molecular weight rather than repeating units.

The term "salt" should be interpreted as any form of the corresponding compound of the present invention, where the compound is in an ionic form, is charged and coupled with an oppositely charged ion (cation or anion), or is in a solution. Also included within this definition are quaternary ammonium salts and complexes of the molecule with other molecules and ions, particularly complexes formed by ionic interactions.

The term "ester" should be interpreted as a corresponding compound formed by a reaction of an acid with the hydroxyl group of the corresponding compound of the present invention.

The term "solvate" should be interpreted as any form of the corresponding compound of the present invention, where the compound is linked to another molecule (usually a polar solvent) by a non-covalent bond, particularly including hydrate and alcoholate such as methanolate.

The term "prodrug" is used in its broad sense and encompasses derivatives that can be converted into the compound of the present invention in vivo. Examples of prodrugs include, but are not limited to, derivatives and metabolites of the corresponding compound of the present invention, including biohydrolyzable moieties such as biohydrolyzable amides, biohydrolyzable esters, biohydrolyzable carbamates, biohydrolyzable carbonates, biohydrolyzable ureides, and biohydrolyzable phosphate analogs. Preferably, the prodrug having a carboxyl functional group is a lower alkyl ester of a carboxylic acid. The carboxylic acid ester is readily esterified from any carboxylic acid moiety present in the molecule. Prodrugs can generally be prepared by known methods, such as those described in "Burger's Medicinal Chemistry and Drug Discovery", sixth edition (Donald J. Abraham ed., 2001, Wiley) and "Design and Applications of Prodrugs" (H. Bundgaard ed., 1985, Harwood Academic Publishers).

The term "tumor" refers to a neoplasm formed by local tissue cells proliferation under the action of various oncogenic factors, and is classified into two major types, namely, benign tumors and malignant tumors according to the cellular characteristics of the neoplasm and the degree of harm to the organism. "Malignant tumor" refers to a disease characterized by uncontrolled growth and spread of malignant cells and tissue infiltration, and determined as a malignant tumor as per pathological examination to meet the "classification of disease and cause of death" criteria promulgated by National Health Commission (formerly Ministry of Health), PRC.

The term "antitumor efficacy" refers to a biological effect that can be represented by a reduction in tumor volume, a reduction in the number of tumor cells, a reduction in the number of metastases, an increase in life expectancy, or an improvement in various physiological symptoms associated with cancerous conditions.

The term "brain tumor" refers to a neoplasm growing in the cranial cavity, also known as intracranial tumor and brain cancer, which may originate from the brain, meninges, nerves, blood vessels, and brain attachments, or metastasis from other tissues or organs of the body invading into the cranium. The most common brain tumor is glioma, which accounts for about ⅓ to ½. For tumors of ectodermal sources, more than half are malignant. Gliomas can be pathologically and clinically classified as: astrocytoma, glioblastoma multiforme, ependymoma, ependymoblastoma, medulloblastoma, oligodendroglioma, and oligodendroblastoma. Other common brain tumors are meningioma, neurilemmoma (90% are acoustic neuromas), pituitary adenoma, craniopharyngioma (the most common intracranial congenital tumor), and the like.

The term "neuroblastoma" refers to a disease that forms malignant (cancerous) cells in the nervous tissue of the adrenal gland, neck, chest, or spinal cord, and is an embryonal tumor of the sympathetic nervous system generated by neuroblasts (pluripotent sympathetic nerve cells). When diagnosed, neuroblastoma is usually metastasized (spread), most commonly, to lymph nodes, bone, bone marrow, liver, and skin.

The term "treating" refers to preventing, curing, reversing, attenuating, alleviating, minimizing, suppressing, arresting, and/or stopping one or more clinical symptoms of a disease after its onset.

The term "preventing" refers to treatment to avoid, minimize, or make difficult the onset or progression of a disease prior to its onset.

The terms "patient" and "subject" and the like are used interchangeably herein and refer to any animal or cell thereof, whether in vitro or in situ, treated according to the method described herein. Specifically, the aforementioned animal includes mammals, for example, rats, mice, guinea pigs, rabbits, dogs, monkeys, or humans, particularly humans.

The disclosures of the various publications, patents, and published patent specifications cited herein are hereby incorporated by reference in their entireties.

The technical schemes of the present invention will be clearly and completely described below with reference to the examples of the present invention, and it is obvious that the described examples are only a part of the examples of the present invention but not all of them. Based on the examples of the present invention, all other examples obtained by those of ordinary skills in the art without creative work shall fall within the protection scope of the present invention.

Example 1

1. Experimental Materials 1.1 Experimental Animals

Species: mouse

Strain: NOD/SCID

Age: 6 to 8 weeks

Sex: female

Number: 120 (100% extra animals)

Source: Shanghai Lingchang Laboratory Animal Co., Ltd.

1.2 Breeding Conditions

Mice were bred in an animal room of the CRO which was designated by JenKem Technology Co., Ltd.

Upon arrival, the animals were transferred from the shipping package to mouse cages and examined. The examinations included appearance, limbs, cavities, and the like, and whether the animal acted abnormally at rest and in motion. The animals were acclimated for 7 days.

Conditions: Mice were housed in clear resin plastic cages (300 mm×180 mm×120 mm) in the animal room, with 5 mice per cage. The mouse cage padding was autoclaved wood chips and corn cob padding, which was replaced twice every week. The room number where the animals were housed was recorded in the experimental record during the experiment. The animal room was equipped with an efficient air filter, with a ventilation rate of 15 to 25 times per hour. The temperature was maintained at 20° C. to 26° C. (68° F. to 79° F.), and the relative humidity was maintained at 40% to 70%. The temperature and humidity were continuously observed and recorded. The lighting conditions were 12/12-hour light (08:00 to 20:00)/dark cycles.

Food and drinking water: Experimental mice had free access to special mouse food (disinfected with irradiation; supplied by Shanghai SLAC Laboratory Animal Co., Ltd., China). Experimental mice also had free access to drinking water treated internally by CRO.

Cage and animal identification: Each animal was assigned a unique number. Before animals were grouped, the mouse cage labels were marked with project number, species/strain, sex, cage number, and animal number.

After the animals were grouped, the cages were marked with group information and information described above by colored labels. The grouping was recorded in the randomization file. The mouse cages were placed on racks to reduce the effect of environmental factors on the experiment.

1.3 Test Compounds

Preparation of the test compounds is as shown in the table below.

TABLE 1

Preparation of compounds

| Test compound | Preparation | Concentration (mg/mL) | Storage condition |
|---|---|---|---|
| Control group | Normal saline | — | 4° C. |
| Temozolomide | 12 mL of physiological saline was added to 24 mg of temozolomide, and the mixture was vortexed to obtain a solution. | 2 | −20° C. |
| PEG-irinotecan | 13.34 mL of physiological saline was added to 40 mg (a whole vial) of PEG-irinotecan, and the mixture was vortexed to obtain a solution. | 3 | −20° C. |
| Irinotecan hydrochloride | 6 mL of physiological saline was added to 18 mg of irinotecan hydrochloride, and the mixture was vortexed to obtain a solution. | 3 | −20° C. |

Note: the PEG-irinotecan described above has the following structure:

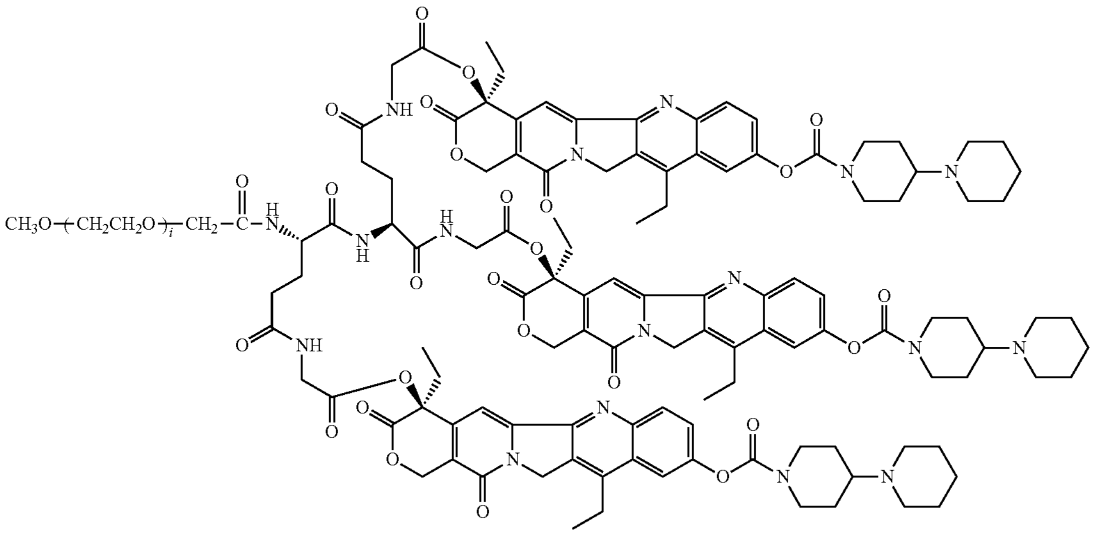

wherein the molecular weight of the PEG moiety is 21000 to 23000.

2. Experimental Methods and Steps 2.1. Cell Culture

SK-N-SH cells were cultured in an EMEM medium containing 10% heat-inactivated fetal bovine serum, 100 μg/mL penicillin, and 100 μg/mL streptomycin (incubator condition: 37° C., 5% CO 2). The cells were subcultured twice a week. The cells in the exponential phase were collected, and counted grafting.

2.2 Tumor grafting and grouping

100 μL of a mixture of EMEM and 50% matrigel containing $5\times10^6$ SK-N-SH cells was grafted subcutaneously at the right abdomen of a mouse, and the tumor growth was observed. 80 animals were randomized according to tumor volume (103 mm 3) by using the grouping randomization method in Excel. This ensured that all groups were comparable at baseline. Each group had 10 tumor-bearing mice.

The treatments of all groups are shown in the table below.

TABLE 2

| Treatment of all groups | | |
|---|---|---|
| Group | Compound | Route of administration, dose, and frequency |
| 1 | Vehicle | PO, QD*5 once every 2 weeks |
| 2 | Temozolomide (TMZ) | 20 mg/kg, PO, QD*5 once every 4 weeks |
| 3 | Irinotecan hydrochloride | 30 mg/kg, IV, 100 μL/min, once every 2 weeks |
| 4 | PEG-irinotecan | 30 mg/kg, IV, 100 μL/min, once every 2 weeks |
| 5 | TMZ + irinotecan hydrochloride | Irinotecan hydrochloride, 30 mg/kg, IV, 100 μL/min, once every 2 weeks + Temozolomide, 20 mg/kg, PO, QD*5 once every 4 weeks |
| 6 | TMZ + PEG-irinotecan | PEG-irinotecan, 30 mg/kg, IV, 100 μL/min, once every 2 weeks + Temozolomide, 20 mg/kg, PO, QD*5 once every 4 weeks |

2.3 Observation

All procedures related to animal handling, care, and treatment in this study were performed according to the assessment of the Institutional Animal Care and Use Committee (IACUC) approved by Shanghai BioDuro Co., Ltd. (the CRO) and followed guidelines of the Association for Assessment and Accreditation of Laboratory Animal Care (AAALAC, accreditation number: 001516). In routine monitoring, the animals were examined that whether any adverse effects of tumor growth and/or treatment on normal behavior were present, such as motility, food and water consumption (by observation only), and body weight gain/loss (the body weight was measured twice a week during the pre-administration phase and daily during the administration phase), eye/hair matting and any other abnormalities.

Tumor volume was measured twice a week using a vernier caliper. The volume (in mm 3) was calculated by the following formula: $V=0.5a\times b^2$, wherein a and b represent the long diameter and short diameter of the tumor, respectively.

$$\text{Relative tumor proliferation rate T/C } \%=T_{RTV}/C_{RTV}\times 100\% \text{ (RTV=Vt/V0)}$$

$$\text{Tumor inhibition rate TGI } \%=(1-T/C)\times 100\%$$

2.4 Statistics

The body weight and tumor volume were compared by using two-way ANOVA analysis. All data were analyzed using GraphPad Prism 5. $p<0.05$ indicates statistical significance.

3. Experimental Results 3.1 Body Weight

Changes in body weight of the animals in each group are shown in Table 3 and FIG. 1.

TABLE 3

| Changes in body weight of the mice in each group | | | |
|---|---|---|---|
| | Animal body weight (g), mean ± standard error | | |
| Days | 1 | 2 | 3 |
| 24 | 21.9 ± 0.3 | 21.7 ± 0.4 | 22 ± 0.4 |
| 27 | 22.5 ± 0.3 | 21.5 ± 0.5 | 21.8 ± 0.5 |
| 31 | 23.6 ± 0.5 | 22 ± 0.6 | 23 ± 0.5 |
| 34 | 23.6 ± 0.5 (n = 9) | 23.7 ± 0.7 (n = 9) | 24.3 ± 0.5 |
| 38 | — (n = 0) | 22.5 ± 0.5 (n = 5) | 23.2 ± 0.4 (n = 8) |
| 41 | — (n = 0) | 23.3 ± 1.1 (n = 2) | 21 (n = 1) |
| 45 | — (n = 0) | — (n = 0) | — (n = 0) |
| 48 | — (n = 0) | — (n = 0) | — (n = 0) |
| 52 | — (n = 0) | — (n = 0) | — (n = 0) |
| | Animal body weight (g), mean ± standard error | | |
| Days | 4 | 5 | 6 |
| 24 | 21.6 ± 0.3 | 22.6 ± 0.4 | 22.1 ± 0.2 |
| 27 | 21.3 ± 0.4 | 22 ± 0.3 | 20.8 ± 0.2 |
| 31 | 21.7 ± 0.4 | 22.2 ± 0.4 | 21 ± 0.4 |
| 34 | 22.2 ± 0.4 | 23.5 ± 0.3 | 21.9 ± 0.2 |
| 38 | 21.5 ± 0.5 | 24.5 ± 0.4 | 21.6 ± 0.3 |
| 41 | 22.1 ± 0.4 | 23 ± 0.8 (n = 4) | 21.5 ± 0.4 |
| 45 | 22.4 ± 0.5 | 23.7 (n = 1) | 22 ± 0.3 |
| 48 | 22.7 ± 0.3 | — (n = 0) | 22.1 ± 0.4 |
| 52 | 23.1 ± 0.4 | — (n = 0) | 22.4 ± 0.3 |

Note:
n = 10 in each group.

3.2 Tumor Volume

Figure 2:
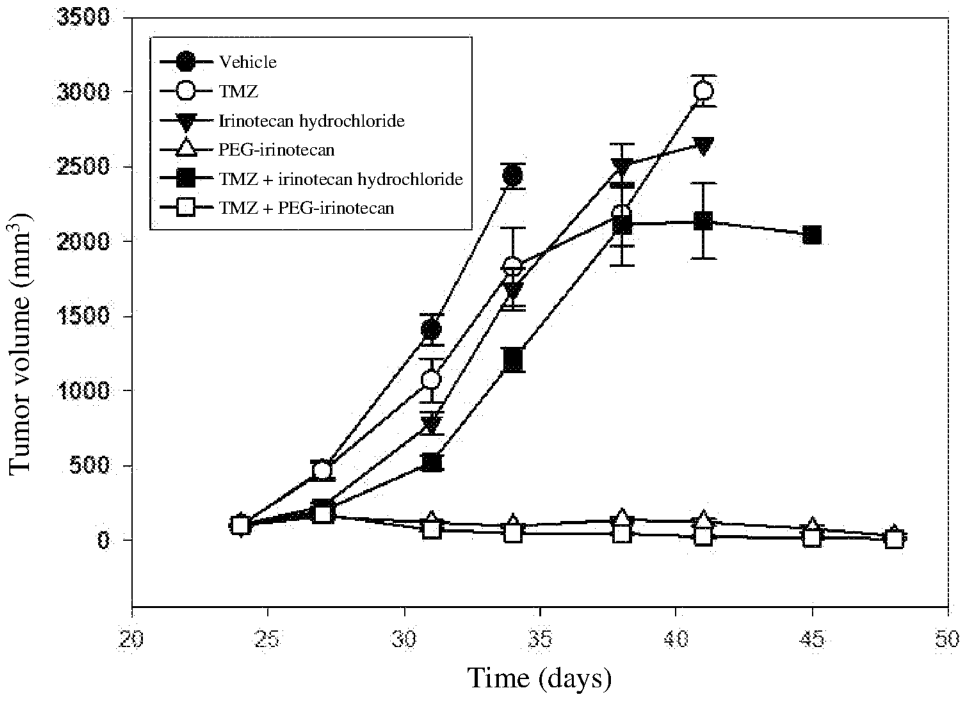
FIG. 2 shows the changes in tumor volume of mice in each group, wherein, the data points represent the mean of the group, and the error bars represent the standard error of the mean (SEM).
Figure 3:
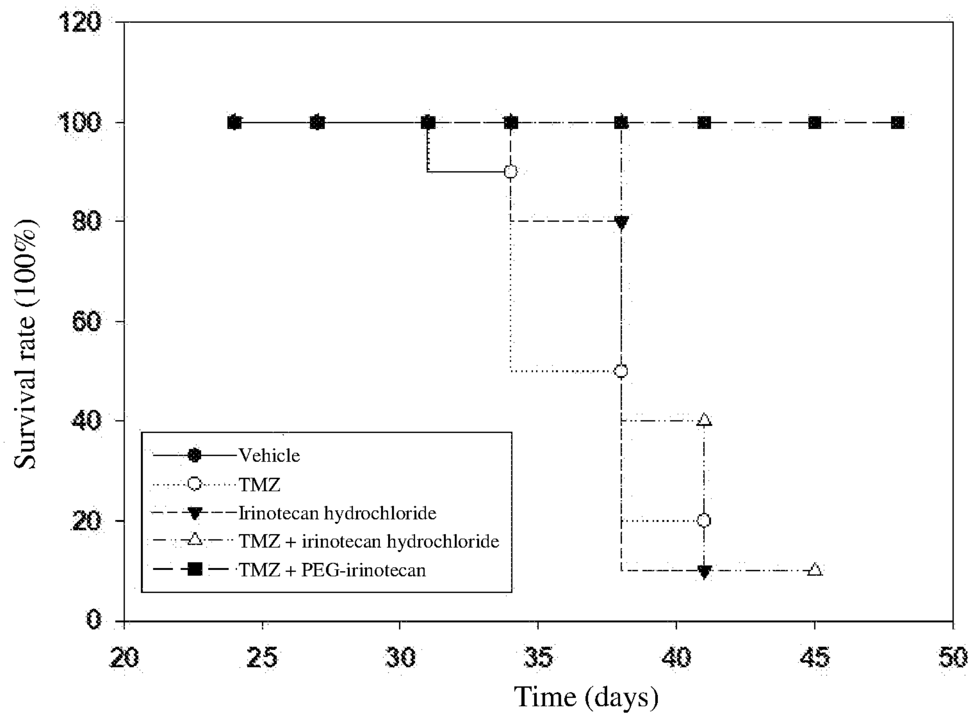
FIG. 3 shows the survival rates of mice in each group, with a total of 10 animals in each treatment group, and the death rate of the animals after administration is related to the tumor inhibition rate.

Tumor volume ($mm^3$) at different time points in each group are shown in Table 4 and FIG. 2.

TABLE 4

| Changes in tumor volume of the mice in each group | | | |
|---|---|---|---|
| | Tumor volume ($mm^3$), mean ± standard error | | |
| Days | 1 | 2 | 3 |
| 24 | 102.5 ± 7 | 102.9 ± 10.8 | 103.3 ± 10.3 |
| 27 | 471.2 ± 53.7 | 462.9 ± 67.1 | 227.7 ± 22.2 |
| 31 | 1408.5 ± 105.2 | 1071 ± 144.9 | 783.5 ± 76.5 |
| 34 | 2438.2 ± 87.4 (n = 9) | 1827.5 ± 262.2 (n = 9) | 1682.5 ± 137.7 |
| 38 | — (n = 0) | 2179.6 ± 209.6 (n = 5) | 2509.5 ± 144.1 (n = 8) |
| 41 | — (n = 0) | 3004.1 ± 100.8 (n = 2) | 2651.9 (n = 1) |
| 45 | — (n = 0) | — (n = 0) | — (n = 0) |
| 48 | — (n = 0) | — (n = 0) | — (n = 0) |
| 52 | — (n = 0) | — (n = 0) | — (n = 0) |

TABLE 4-continued

Changes in tumor volume of the mice in each group

| | Tumor volume ($mm^3$), mean ± standard error | | |
|---|---|---|---|
| Days | 4 | 5 | 6 |
| 24 | 103.4 ± 6.8 | 103.3 ± 8.6 | 102.2 ± 11.4 |
| 27 | 158.6 ± 19.9 | 195.6 ± 22.2 | 174.4 ± 20.3 |
| 31 | 120.4 ± 12.9 | 519.3 ± 46.2 | 68.7 ± 10.4 |
| 34 | 95.7 ± 17 | 1207.8 ± 78.8 | 48.5 ± 6.2 |
| 38 | 138.3 ± 21.3 | 2110.9 ± 274.1 | 44.2 ± 13 |
| 41 | 122 ± 24.2 | 2133.8 ± 251.7 (n = 4) | 24.7 ± 9.5 |
| 45 | 76.5 ± 22.6 | 2046.4 (n = 1) | 16.3 ± 7.4 |
| 48 | 30.1 ± 11.7 | — (n = 0) | 10.5 ± 5.7 |
| 52 | 21.6 ± 8.7 | — (n = 0) | 8.3 ± 4.5 |

Note:
n = 10 in each group.

3.3 Tumor Growth Inhibitory Effect

Tumor growth inhibitory effects in each group are shown in Table 5.

TABLE 5

Antitumor activity in each group

| | | | D 34 | | |
|---|---|---|---|---|---|
| Group | TV ($mm^3$)[a] | TV ($mm^3$)[b] | T/C (%) | 1 - T/C (%) | Significant TV[c] |
| 1 | 102.5 ± 7 | 2438.2 ± 87.4 | — | — | — |
| 2 | 102.9 ± 10.8 | 1827.5 ± 262.2 | 74.96 | 25.04 | *** |
| 3 | 103.3 ± 10.3 | 1682.5 ± 137.7 | 69.01 | 30.99 | *** |
| 4 | 103.4 ± 6.8 | 95.7 ± 17 | 3.92 | 96.08 | *** |
| 5 | 103.3 ± 8.6 | 1207.8 ± 78.8 | 49.54 | 50.46 | *** |
| 6 | 102.2 ± 11.4 | 48.5 ± 6.2 | 1.99 | 98.01 | *** |

Note:
[a]Tumor volume on day 24;
[b]Tumor volume on day 34;
[c]On day 34, all groups were compared with the vehicle group.

4. Results and Discussion

This study tested the therapeutic effect of PEG-irinotecan, temozolomide, and the combination of temozolomide and PEG-irinotecan on SK-N-SH in the nude mouse subcutaneous tumor model.

The body weights of each group at different time points after tumor grafting are shown in Table 3 and FIG. 1. The body weights of each group were stable during the study with no significant differences, indicating that the various regimens in this study have no significant toxic or side effects on the mice.

In these 6 regimens, Groups 4 and 6 had extremely significant therapeutic efficacy, with tumor inhibition rates being 96.1% and 98.0%, respectively (P<0.001).

Groups 2, 3, and 5 had mild tumor inhibition efficacy, with tumor inhibition rates of being 25.0%, 31.0%, and 50.5%, respectively (P<0.001). The data from these groups show enhanced tumor inhibition efficacies of the combination therapies compared with the monotherapies.

In conclusion, the combination therapy groups show extremely potent therapeutic efficacy in SK-N-SH in vivo subcutaneous tumor model of the study.

The above description is only for the purpose of illustrating the preferred examples of the present invention, and is not intended to limit the scope of the present invention. Any modifications, equivalents, and the like made without departing from the spirit and principle of the present invention shall fall in the protection scope of the present invention.

The foregoing examples and methods described herein may vary based on the abilities, experience, and preferences of those skilled in the art.

The certain order in which the steps of the method are listed in the present invention does not constitute any limitation on the order of the steps of the method.

The invention claimed is:

1. A method for treating neuroblastoma, comprising a step of administering a pharmaceutical composition to a subject in need thereof, wherein the pharmaceutical composition comprises the following as active ingredients:

(1) a polyethylene glycol-modified camptothecin derivative which has the following structure:

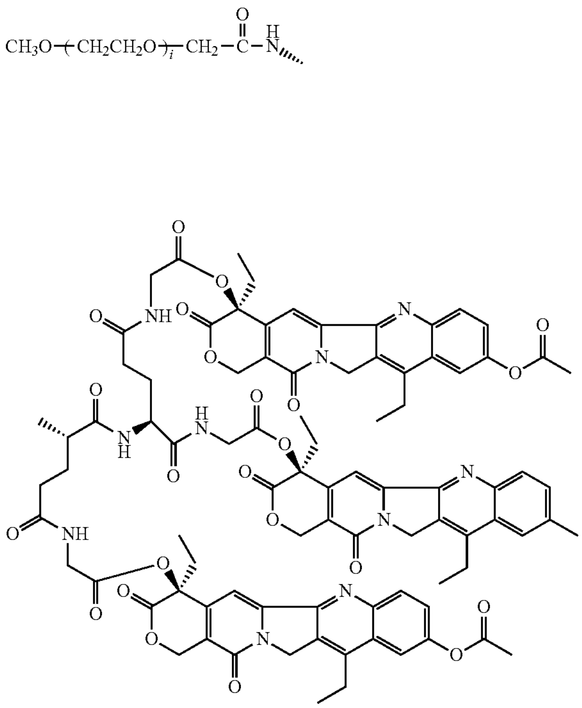

-continued

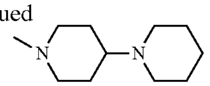

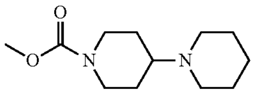

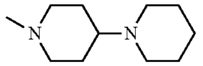

wherein, i is an integer of 10 to 1500, and (2) temozolomide or a pharmaceutically acceptable salt thereof.

2. The method of claim 1, wherein the polyethylene glycol moiety of

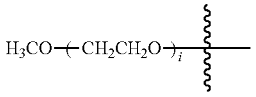

has a molecular weight of 20000 to 40000 Daltons.

(2) the temozolomide or the pharmaceutically acceptable salt thereof.

5. The method of claim 4, wherein the polyethylene glycol moiety of

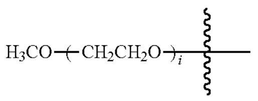

has a molecular weight of 20000 to 40000 Daltons.

6. The method of claim 4, wherein the polyethylene glycol moiety of

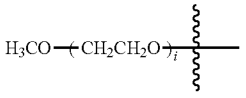

has a molecular weight of 21000 to 23000 Daltons.

7. A method for treating neuroblastoma, comprising a step of administering a polyethylene glycol-modified camptothecin derivative to a subject in need thereof, wherein the polyethylene glycol-modified camptothecin derivative has the following structure:

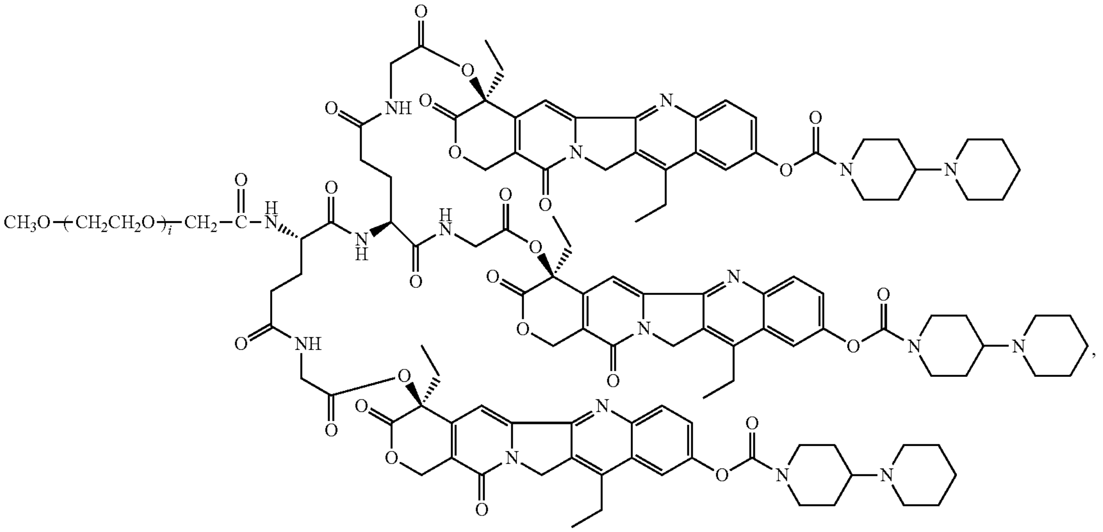

3. The method of claim 1, wherein the polyethylene glycol moiety of

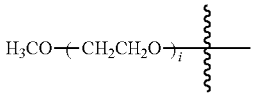

has a molecular weight of 21000 to 23000 Daltons.

4. The method of claim 1, wherein the active ingredients of the pharmaceutical composition consist of the following:

(1) the polyethylene glycol-modified camptothecin derivative, and wherein, i is an integer of 10 to 1500.

8. The method of claim 7, wherein the polyethylene glycol moiety of

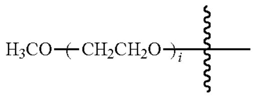

has a molecular weight of 20000 to 40000 Daltons.

9. The method of claim 7, wherein the polyethylene glycol moiety of

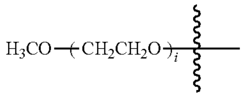
has a molecular weight of 21000 to 23000 Daltons.
* * * * *